United States Patent
Halliyal et al.

(10) Patent No.: US 6,828,162 B1
(45) Date of Patent: Dec. 7, 2004

(54) SYSTEM AND METHOD FOR ACTIVE CONTROL OF BPSG DEPOSITION

(75) Inventors: Arvind Halliyal, Sunnyvale, CA (US); Bhanwar Singh, Morgan Hill, CA (US); Michael K. Templeton, Atherton, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 42 days.

(21) Appl. No.: 09/894,434

(22) Filed: Jun. 28, 2001

(51) Int. Cl.[7] .............................................. H01L 21/00
(52) U.S. Cl. .......................................... 438/14; 438/428
(58) Field of Search ................................ 438/428, 436, 438/438, 432, 645, 14, 18, 16

(56) References Cited

U.S. PATENT DOCUMENTS

| | | | | |
|---|---|---|---|---|
| 4,476,154 A | * | 10/1984 | Iesaka et al. ................ | 438/438 |
| 5,748,318 A | * | 5/1998 | Maris et al. ................. | 356/630 |
| 6,211,035 B1 | * | 4/2001 | Moise et al. ................. | 438/396 |

FOREIGN PATENT DOCUMENTS

JP          3-020059      *  1/1991    ........... H01L/21/66

* cited by examiner

Primary Examiner—W. David Coleman
(74) Attorney, Agent, or Firm—Amin & Turocy, LLP

(57) ABSTRACT

A system for monitoring and controlling a boron phosphorous doped silicon oxide (BPSG) deposition and reflow process is provided. The system includes one or more light sources, each light source directing light to one or more portions of a wafer upon which BPSG is deposited. Light reflected from the BPSG is collected by a measuring system, which processes the collected light. Light passing through the BPSG may similarly be collected by the measuring system, which processes the collected light. The collected light is indicative of the conformality of the BPSG deposition of the respective portions of the wafer. The measuring system provides BPSG deposition related data to a processor that determines the BPSG deposition of the respective portions of the wafer. The system also includes a plurality of reflow controlling devices, each such device corresponding to a respective portion of the wafer and providing for the heating and/or cooling thereof. The processor selectively controls the reflow controlling devices so as to regulate temperature of the respective portions of the wafer.

15 Claims, 13 Drawing Sheets

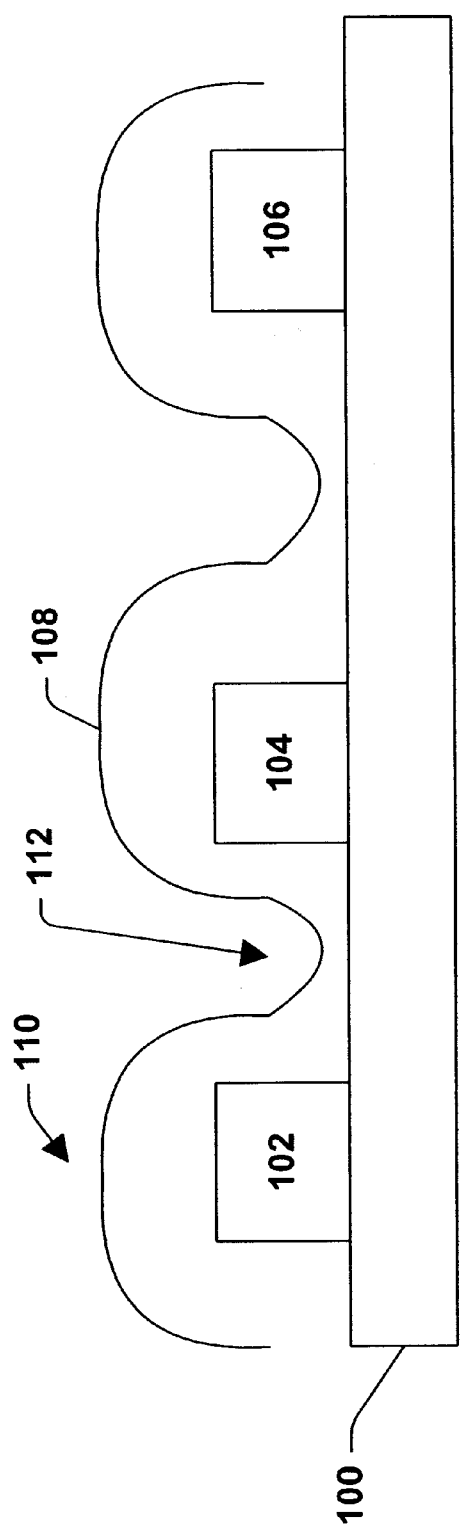

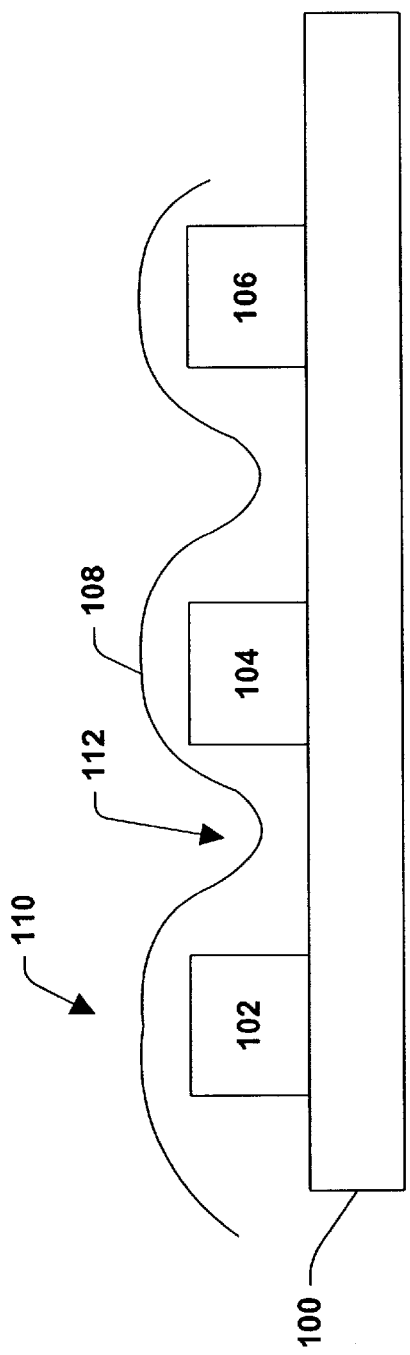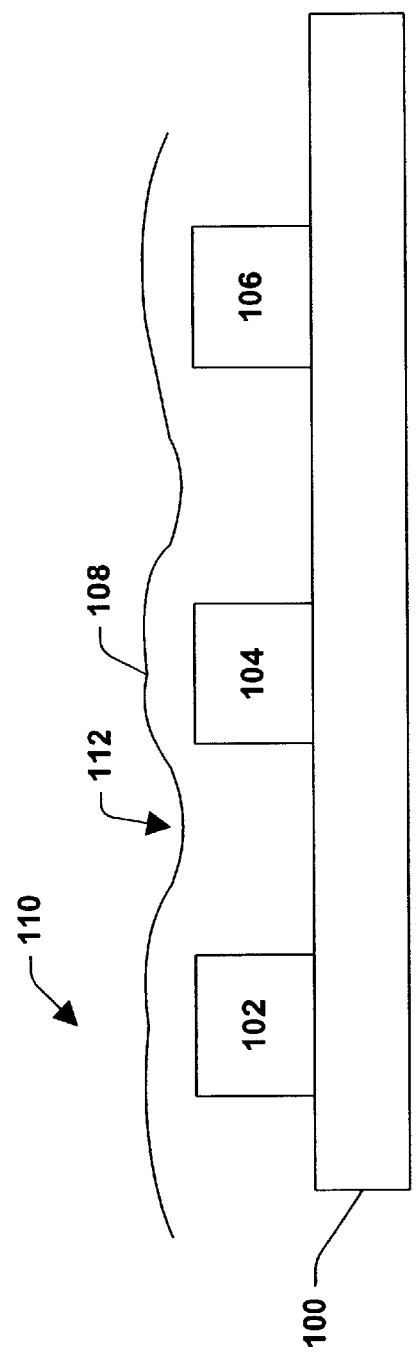

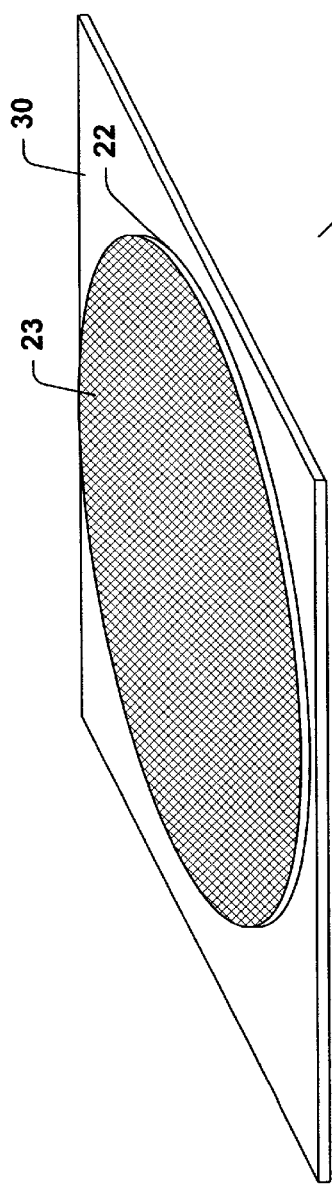
Fig. 6
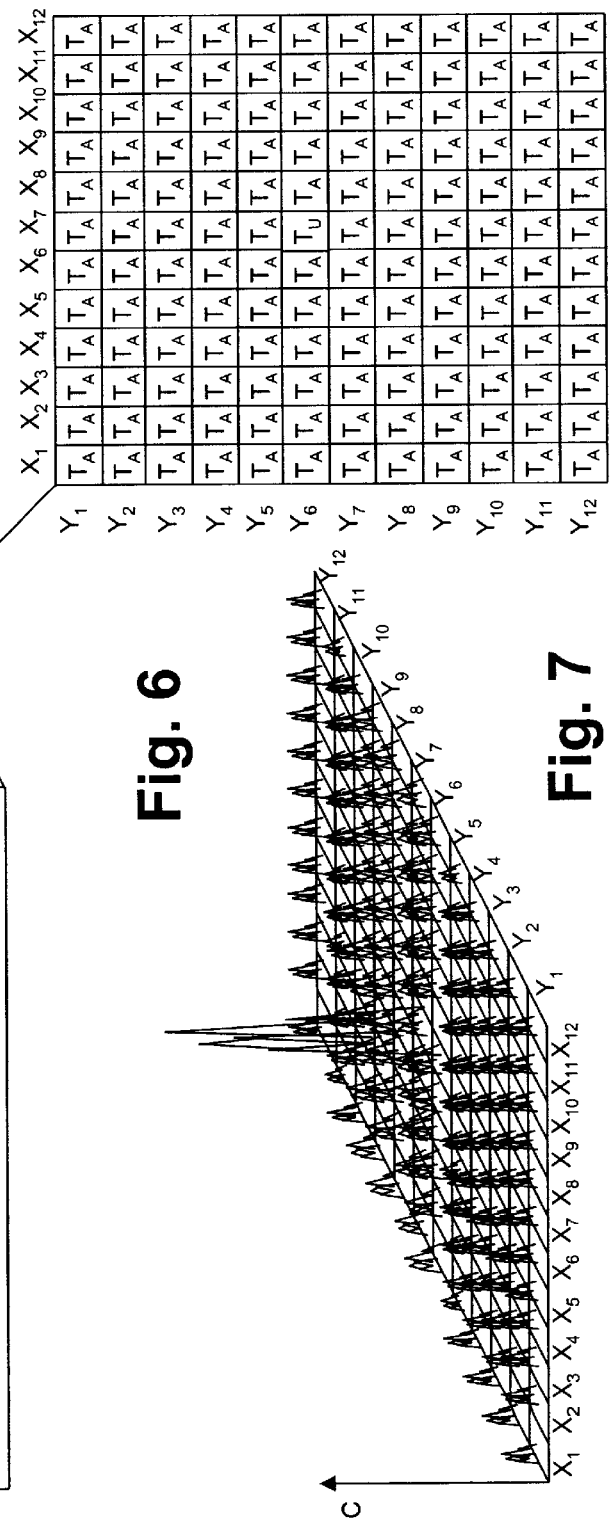
Fig. 8
Fig. 7 ism and METHOD FOR ACTIVE
SYSTEM AND METHOD FOR ACTIVE CONTROL OF BPSG DEPOSITION

TECHNICAL FIELD

The present invention generally relates to semiconductor processing, and in particular to a system for monitoring and controlling boron phosphorous doped silicon oxide (BPSG) deposition and reflow.

BACKGROUND

In the semiconductor industry, there is a continuing trend toward higher device densities. To achieve these high densities there have been, and continue to be, efforts toward scaling down device dimensions (e.g., at sub-micron levels) on semiconductor wafers and to increase the number of layers of such devices on a chip. In order to accomplish such high device packing densities, smaller and smaller features sizes are required. This may include the width and spacing of interconnecting lines, spacing and diameter of contact holes, and the surface geometry, such as corners and edges, of various features. The smaller features are separated by layers of thin dielectric films (e.g. BPSG). But the deposition of the thin dielectric film BPSG is not conformal, which negatively impacts the ability to achieve desired feature sizes and packing densities.

The process of manufacturing semiconductors, or integrated circuits (commonly called ICs, or chips), typically consists of more than a hundred steps, during which hundreds of copies of an integrated circuit may be formed on a single wafer. Generally, the process involves creating several patterned layers on and into the substrate that ultimately forms the complete integrated circuit. This layering process creates electrically active regions in and on the semiconductor wafer surface. Thin dielectric films, such as BPSG, are used in fabricating chips.

The requirement of small features with close spacing between adjacent features requires sophisticated manufacturing techniques, including high-resolution photolithographic processes, and controlling dielectric layer deposition. Fabricating a semiconductor using such sophisticated techniques may involve a series of steps including cleaning, thermal oxidation or deposition, masking, developing, etching, baking and doping.

Wafers may be pre-cleaned using, for example, high-purity, low-particle chemicals. The silicon wafers may be heated and exposed to ultra-pure oxygen in diffusion furnaces under carefully controlled conditions to form a silicon dioxide film of uniform thickness on the surface of the wafer. Once the wafer is clean, layers of oxide and photo resist can be applied. The masking step is used to protect one area of the wafer while working on another area. This process is referred to as photolithography or photo-masking. A photo resist, or light-sensitive film, is applied to the wafer, giving it characteristics similar to a piece of photographic paper. A photo aligner aligns the wafer to a mask, and then projects an intense light through the mask and through a series of reducing lenses, exposing the photo resist with the mask pattern. Precise alignment of the wafer to the mask prior to exposure is critical.

In the developing step, the wafer is then "developed", wherein selected portions of the photo resist are hardened. The portions of the photo resist that were not hardened may be removed, exposing the oxide layer beneath. Once the oxide is exposed, the wafer may be etched, to remove undesired areas of oxide. The etching may be accomplished, for example, by a chemical solution or plasma (gas discharge). The photo resist remaining after the undesired oxide has been removed is then removed using additional chemicals or plasma to reveal the desired pattern in the oxide. The wafer is then inspected to ensure the image transfer from the mask to the top layer is correct.

In the doping step, atoms with one less electron than silicon (e.g. boron), or one more electron than silicon (e.g. phosphorous), are introduced into the area exposed by the etch process to alter the electrical character of the silicon. These areas are called P-type (boron) or N-type (phosphorous) to reflect their conducting characteristics. The thermal oxidation, masking, etching and doping steps may be repeated several times until the last "front end" layer is completed (e.g. all active devices have been formed).

ICs may consist of more than one layer, the layers being separated by dielectric layers. Irregularities in the dielectric layers may create problems, like electrical shorting between features and/or layers, for example. Further, dielectric layers that are too thick may prevent achieving desired packing densities and may reduce the number of layers that may be deposited on an IC. Further still, dielectric layers with irregular surfaces may require more material to be deposited to fabricate subsequent layers than would be required by a more uniform surface.

BPSG may be deposited, for example, by a plasma or vapor deposition process. Ideally, such a process would deposit a uniform layer of BPSG on a wafer, but variations occur both between fabrication runs and within wafers. Since there since there may be irregularities and since uniformity in BPSG layer deposition is desired, the non-conformal deposition of BPSG may require local planarization to achieve the desired surface plane.

Thus, an efficient system and/or method to monitor and control the BPSG deposition and reflow for local planarization process is desired to increase chip quality.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention provides a system that facilitates controlling boron phosphorous doped silicon oxide (BPSG) deposition and reflow for local planarization. An exemplary system may employ one or more light sources arranged to project light onto one or more portions of a wafer upon which BPSG is deposited and one or more light sensing devices (e.g. photo detector, photodiode) for detecting light reflected by, and/or allowed to pass through the BPSG. The light reflected from, and/or passing through the BPSG is indicative of at least one parameter of the BPSG deposition and reflow for local planarization process (e.g.uniformity of surface).

A plurality of reflow controlling components are arranged to correspond to a particular wafer portion. The reflow controlling components may be, for example, heat lamps, baking plates, and/or fluid conducting apparatus. It is to be appreciated by one skilled in the art that any suitable reflow controlling component may be employed with the present invention. Each reflow controlling component may be responsible for heating and/or cooling one or more particular wafer portions. The reflow controlling components are selectively driven by the system to regulate the reflow of BPSG for local planarization on a wafer portion. The BPSG deposition and reflow is monitored by the system by analyzing the light reflected from and/or passing through the wafer. As a result, more optimal BPSG deposition and reflow is achieved by controlling the temperatures applied to the portions of the wafer, which in turn increases chip quality.

An aspect of the present invention provides a system for monitoring and controlling boron phosphorous doped silicon oxide (BPSG) deposition and reflow comprising: at least one reflow controlling component operative to control the temperature of at least one portion of a wafer; a reflow controlling component driving system for driving the at least one reflow controlling component; a system for directing light to the at least one portion of the wafer; a measuring system for measuring BPSG deposition parameters based on light reflected from the at least one portion of the wafer; and a processor operatively coupled to the measuring system and the reflow controlling component driving system, the processor receiving BPSG deposition data from the measuring system and the processor using the data to at least partially base control of the at least one reflow controlling component so as to regulate the temperature of the at least one portion of the wafer.

Another aspect of the present invention provides a method for monitoring and controlling BPSG deposition and reflow comprising: defining a wafer as a plurality of portions; depositing BPSG on the wafer; directing light onto at least one of the portions; collecting light reflected from the at least one portion; analyzing the reflected light to determine the BPSG deposition on the at least one portion; and controlling a reflow controlling component to regulate the BPSG deposition and reflow of the at least one portion.

Yet another aspect of the present invention provides a method for monitoring and controlling a BPSG deposition and reflow process comprising: partitioning a wafer into a plurality of grid blocks; using a plurality of reflow controlling components to control the temperature of the wafer, each reflow controlling component functionally corresponding to a respective grid block; determining the BPSG conformality of one or more portions of the BPSG, each portion corresponding to a respective grid block; and using a processor to coordinate control of the plurality of reflow controlling components, respectively, in accordance with determined BPSG conformality in the respective portions of the BPSG.

Still yet another aspect of the present invention provides a system for monitoring and controlling a BPSG deposition and reflow process comprising: means for partitioning a wafer into a plurality of grid blocks; means for sensing BPSG deposition of at least one of the plurality of portions of the wafer; means for controlling the temperature of the respective wafer portions; and means for selectively controlling the means for controlling the temperature to regulate the temperature of the respective wafer portions.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1 illustrates an initial non-conformal deposition of BPSG;

FIG. 2 illustrates a BPSG layer with improved conformality after reflow in accordance with an aspect of the present invention;

FIG. 3 illustrates a BPSG layer after further reflow in accordance with an aspect of the present invention;

FIG. 6 is a perspective illustration of a substrate (including BPSG layer) that may be processed accordance with the present invention;

FIG. 7 is a representative three-dimensional grid map of a wafer illustrating BPSG conformality measurements taken at grid blocks of the grid map in accordance with the present invention;

FIG. 8 is a BPSG conformality measurement table correlating the measurements of FIG. 7 with desired values for conformality measurements in accordance with the present invention;

DETAILED DESCRIPTION

Figure 4:
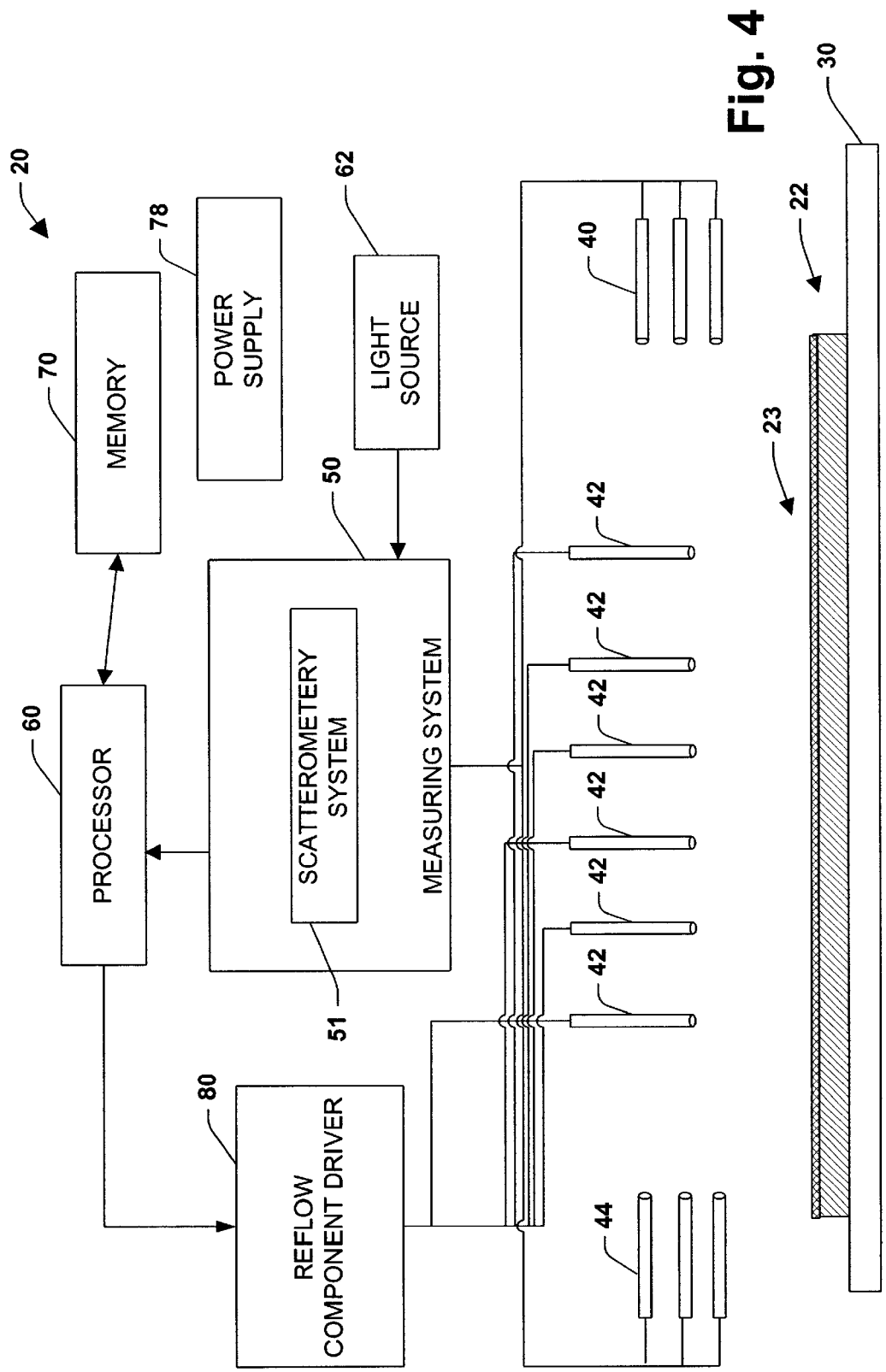
FIG. 4 is a schematic block diagram of a system for monitoring and controlling the deposition and reflow of BPSG in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that the present invention may be practiced without these specific details. In other instances, well-known structures and devices are shown in block diagram form in order to facilitate description of the present invention.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed).

Referring initially to FIG. 1, a wafer 100, with a plurality of features 102, 104 and 106 is illustrated. The features 102, 104 and 106 have been covered by a layer of boron phosphorous doped silicon oxide (BPSG) 108. The BPSG 108 can be deposited using techniques well known in the art. As can be seen, the layer of BPSG 108 has been deposited in a non-conformal manner. For example, there are peaks 110 and valleys 112 in the BPSG 108, creating a non-uniform surface in the BPSG 108. The non-uniform surface is undesirable because it may cause difficulties in subsequent processing of the wafer 100 (e.g. material waste, undesired electrical properties, expanded layer sizes). Thus, a system and method to reduce the nonconformality of the BPSG 108 is required.

Referring now to FIG. 2, the BPSG 108 has been reheated to cause a reflow. The reflow has reduced the height of the peaks 110 and has reduced the depths of the valleys 112 in the BPSG 108. But the reflow may not have produced a BPSG 108 layer of acceptable conformality or surface uniformity. Light directed incident to the surface of the wafer 22 will reflect at different angles from the BPSG 108, including reflections from the peaks 110 and valleys 112. Such reflections can be employed to determine BPSG 108 layer conformality. Thus, turning to FIG. 3, the BPSG 108 has been reheated one or more further times to cause one or more further reflows, which have further reduced the height of the peaks 110, and the depths of the valleys 112. A system for monitoring the conformality of the BPSG 108, via measuring light reflected from the surface of the BPSG can be employed to determine when an acceptable BPSG 108 surface has been achieved through the iterations of reheating and reflow.

Thus, referring now to FIG. 4, a system 20 for controlling BPSG 23 deposition on a wafer 22 is shown. The system 20 further includes a plurality of reflow controlling components 42 that are selectively controlled by the system 20 so as to facilitate controlled heating and/or cooling of the wafer 22, which is supported on a chuck 30. One or more light sources 44 project light onto respective portions of the wafer 22. Light reflected by, and/or passed through, the BPSG 23 is collected by one or more light detecting components 40, and processed by a grating parameter measuring system 50 to measure at least one parameter relating to the BPSG 23 deposition. The reflected and/or passed through light is processed with respect to the incident light in measuring the various parameters.

The measuring system 50 includes a scatterometry system 51. It is to be appreciated that any suitable scatterometry system may be employed to carry out the present invention and such systems are intended to fall within the scope of the claims appended hereto. Scatterometry systems are well known in the art, and therefore further discussion related thereto is limited for sake of brevity. Sample scatterometry systems are briefly described in association with FIG. 10 and FIG. 11.

A source of light 62 (e.g., a laser) provides light to the one or more light sources 44 via the measuring system 50. Preferably, the light source 62 is a frequency stabilized laser, however, it will be appreciated that any laser or other light source (e.g., laser diode or helium neon (HeNe) gas laser) suitable for carrying out the present invention may be employed. One or more light detecting components 40 (e.g., photo detector, photo diodes) collect light reflecting from the BPSG 23.

A processor 60 receives the measured data from the measuring system 50 and determines the conformality of the surface of the respective portions of the wafer 22. The processor 60 is operatively coupled to the measuring system 50 and is programmed to control and operate the various components within the system 20 in order to carry out the various functions described herein. The processor, or CPU 60, may be any of a plurality of processors, such as the AMD K7 and other similar and compatible processors. The manner in which the processor 60 can be programmed to carry out the functions relating to the present invention will be readily apparent to those having ordinary skill in the art based on the description provided herein.

A memory 70, which is operatively coupled to the processor 60, is also included in the system 20 and serves to store program code executed by the processor 60 for carrying out operating functions of the system 20 as described herein. The memory 70 also serves as a storage medium for temporarily storing information such as reflow temperature, reflow temperature tables, BPSG 23 coordinate tables, BPSG 23 surface readings, BPSG 23 surface shapes, scatterometry information, and other data that may be employed in carrying out the present invention.

A power supply 78 provides operating power to the system 20. Any suitable power supply (e.g., battery, line power) may be employed to carry out the present invention.

The processor 60 is also coupled to a reflow component driving system 80 that drives the reflow controlling components 42. The reflow component driving system 80 is controlled by the processor 60 to selectively vary the output of the respective reflow controlling components 42. Each respective portion of the wafer 22 is associated with a corresponding reflow controlling component 42. The processor 60 monitors the BPSG 23 deposition of one or more portions of the BPSG 23 deposited on the wafer 22, and selectively regulates the temperature of each portion via the corresponding reflow controlling components 42. As a result, the system 20 provides for regulating the BPSG deposition and reflow on the wafer 22, which in turn improves chip quality by enabling more uniform BPSG 23 layers.

Figure 5:
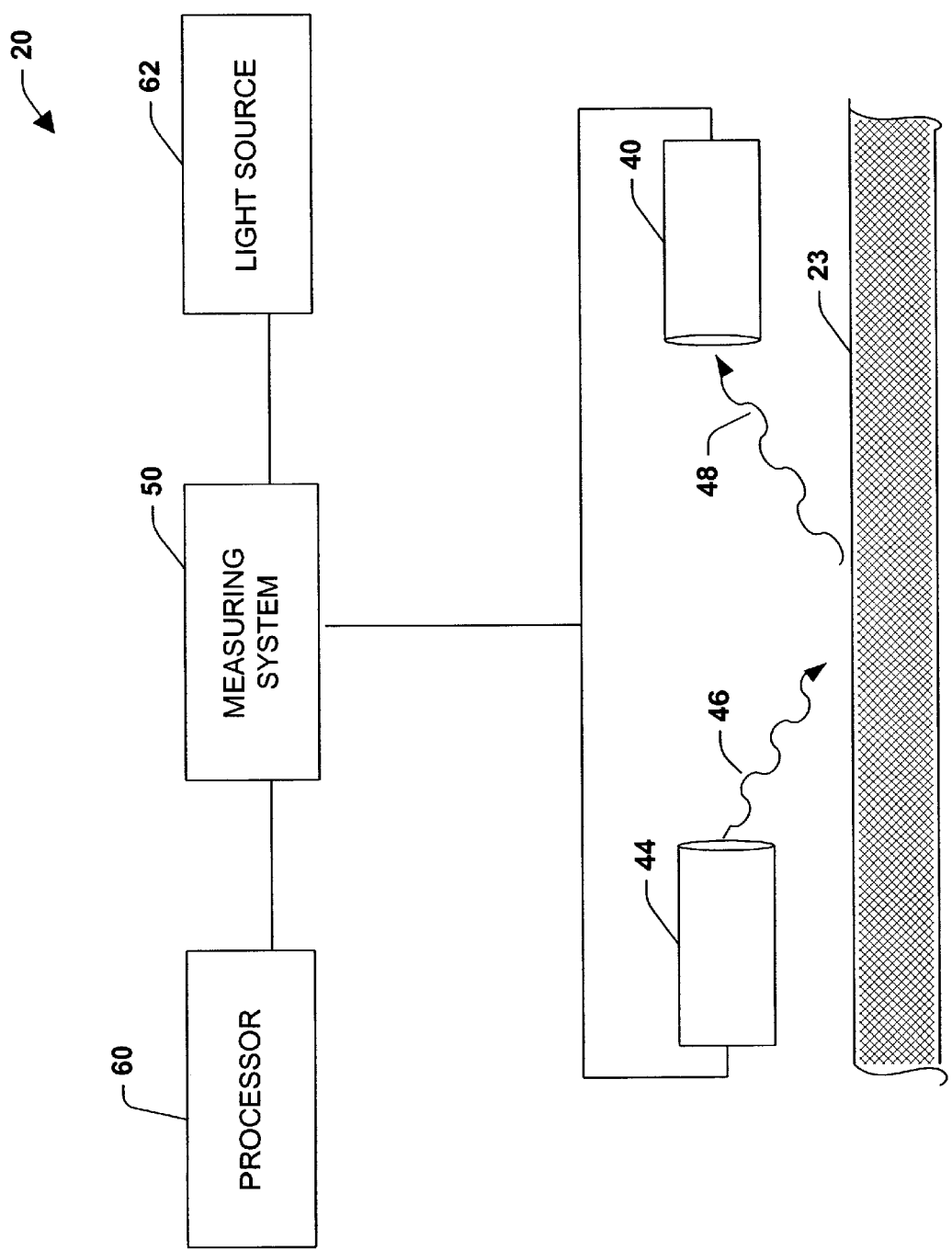
FIG. 5 is a partial schematic block diagram of the system of FIG. 4 being employed in connection with monitoring and controlling the deposition and reflow of BPSG in accordance with the present invention.

FIG. 5 illustrates the system 20 being employed to measure the BPSG 23 deposition and reflow at a particular portion of the BPSG 23. The temperature of the portion of the wafer 22 upon which the BPSG 23 is deposited will have an impact on the BPSG 23 deposition and reflow. The light source 44 directs a light 46 incident to the surface of the wafer 22. The reflected light 48 from the surface of the BPSG 23 will vary (e.g., variations in intensity and/or phase)in accordance with the regularity of the surface of the BPSG 23. The one or more light detecting components 40 collect the reflected light 48, pass the collected light, and/or data concerning the collected light, to the measuring system 50, which processes the reflected light 48 and/or data concerning the reflected light 48 in accordance with suitable techniques (e.g., scatterometry, spectroscopic ellipsometry) to provide the processor 60 with data corresponding to the BPSG 23 deposition and reflow. By feeding back reflected light scatterometry information concerning the BPSG 23 surface during deposition and/or reflow, smoother BPSG 23 surfaces may be fabricated by enabling localized reflow control thus enhancing chip quality.

Turning now to FIGS. 6–8 a chuck 30 is shown in perspective supporting a wafer 22 whereupon a BPSG 23 layer may be deposited. The wafer 22 may be divided into a grid pattern as shown in FIG. 8. Each grid block (XY) of the grid pattern corresponds to a particular portion of the wafer 22. Each portion is individually monitored for BPSG deposition, and each portion is individually controlled for deposition and/or reflow.

In FIG. 7, one or more portions of the wafer 22 ($X_1Y_1 \ldots X_{12}, Y_{12}$) are being monitored for BPSG deposition and/or reflow using reflective and/or passed through light, the measuring system 50 and the processor 60. The BPSG 23 deposition measurements for each portion are shown. As can be seen, the BPSG 23 deposition reading at coordinate $X_7Y_6$ is substantially higher than the BPSG 23 deposition readings of the other portions XY. Such a reading can indicate that the surface conformality at that portion of the wafer 22 is unacceptable, and that further reflow is required to produce a desired uniformity in the BPSG 23 layer. It is to be appreciated that although FIG. 7 illustrates the wafer 22 being mapped (partitioned) into 144 grid block portions, the wafer 22 may be mapped with any suitable number of portions. Although the present invention is described with respect to one reflow controlling component 42 corresponding to one grid block XY, it is to be appreciated that any suitable number of reflow controlling components 42 corresponding to any suitable number of wafer 22 portions may be employed.

FIG. 8 is a representative table of BPSG 23 deposition measurements taken for the various grid blocks that have been correlated with acceptable BPSG 23 deposition values for the portions of the wafer 22 mapped by the respective grid blocks. As can be seen, all the grid blocks, except grid block $X_7Y_6$, have BPSG 23 deposition measurements corresponding to an acceptable BPSG 23 deposition table value ($T_A$) (e.g., are within an expected range of BPSG 23 deposition measurements), while grid block $X_7Y_6$ has an undesired BPSG 23 deposition table value ($T_U$). Thus, the processor 60 has determined that an undesirable BPSG 23 deposition condition exists at the portion of the wafer 22 mapped by grid block $X_7Y_6$. Accordingly, the processor 60 can drive at least the reflow controlling component $42_{7,6}$, which corresponds to the portion of the wafer 22 mapped at grid block $X_7Y_6$, to bring the temperature of this portion of the wafer 22 to a level required to cause localized reflow. It is to be appreciated that the reflow controlling components 42 may be driven so as to increase, and/or decrease, the temperature of the respective wafer 22 portions as desired. Thus, a more uniform BPSG 23 layer may be formed via iterations of heating leading to reflow. Localized control of such heating and reflow can reduce undesired side effects of heating the entire wafer 22 when only a portion of the wafer 22 suffers from an undesirable BPSG 23 conformality condition.

Figure 9:
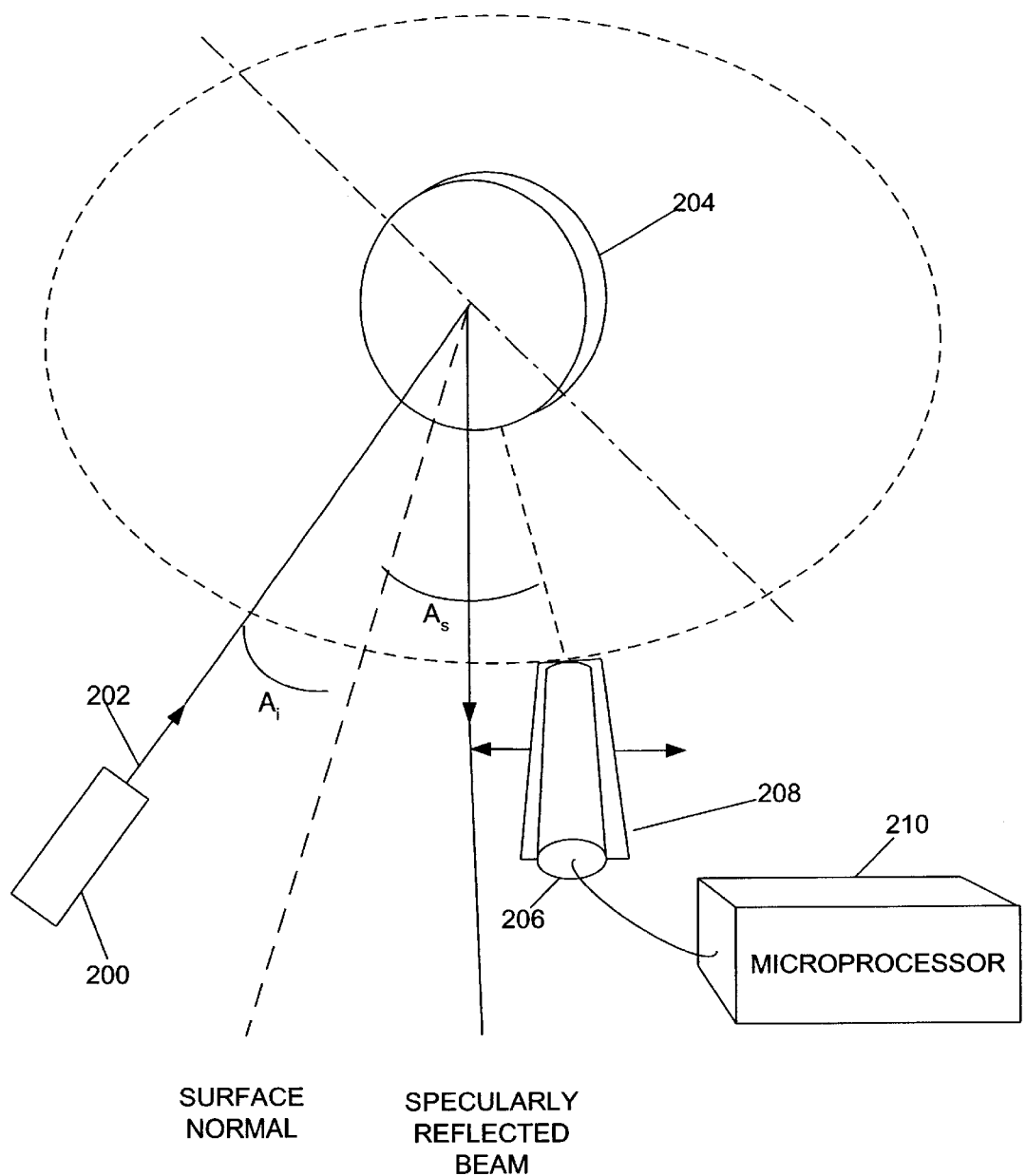
FIG. 9 illustrates an exemplary scatterometry system collecting reflected light in accordance with an aspect of the present invention.

FIG. 9 illustrates an exemplary scatterometry system collecting reflected light. Light from a laser 200 is brought to focus in any suitable well-known manner to form a beam 202. A sample, such as a wafer 204 is placed in the path of the beam 202 and a photo detector or photo multiplier 206 of any suitable well-known construction. Different detector methods may be employed to determine the scattered power.

To obtain a grating pitch, the photo detector or photo multiplier 206 may be mounted on a rotation stage 208 of any suitable well-known design. A microprocessor 210, of any suitable well-known design, may be used to process detector readouts, including, but not limited to, angular locations of different diffracted orders leading to diffraction grating pitches being calculated. Thus, light reflected from the sample 204 may be accurately measured. Accurately measuring the light reflected from the sample 204 enables determining whether the BPSG 23 layer deposition and reflow process has produced a BPSG 23 layer with a desired conformality. When the sample 204 includes the BPSG 23 layer, light reflected from the surface of the BPSG 23 can produce patterns that facilitate determining whether a desired conformality has been achieved in the surface of the BPSG 23.

Figure 10:
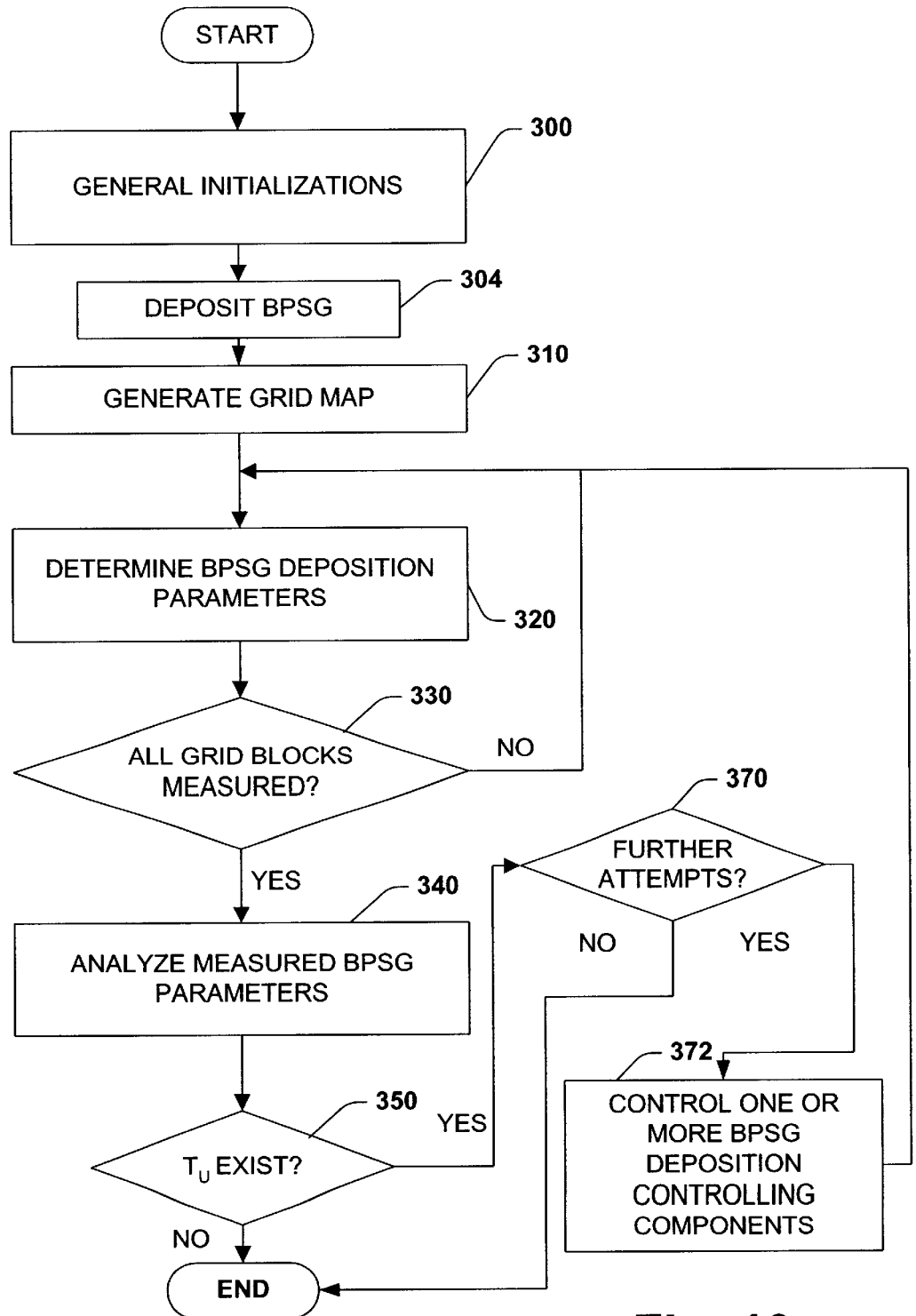
FIG. 10 is a flow diagram illustrating one specific methodology for carrying out the present invention.

FIG. 10 is a flow diagram illustrating one particular methodology for carrying out the present invention. In step 300, general initializations are made to a system for monitoring and controlling BPSG deposition and reflow. At step 304, the initial layer of BPSG is deposited on a wafer to be processed. At step 310, a portion of the wafer to be processed is partitioned into a plurality of grid blocks "XY". At step 320, BPSG deposition determinations are made with respect to the various wafer portions mapped by the respective grid blocks XY. In step 330, a determination is made concerning whether all grid block measurements have been taken. If no, the control returns to step 320. If yes, at step 340, the determined BPSG deposition values are analyzed for acceptable BPSG deposition levels for the respective portions of the wafer. In step 350, a determination is made concerning whether any BPSG deposition values are not acceptable. If all BPSG deposition values are acceptable, this particular iteration of the present methodology ends. If unacceptable BPSG deposition values are found for any of the grid blocks, then at step 370 a determination is made concerning whether further attempts to reheat and reflow the BPSG are to be made. If the determination at step 370 is NO, then the portion of the wafer where the unacceptable BPSG deposition condition exists may be marked for further processing and/or destruction. The method may also send alarms to other methods and/or apparatus involved in subsequently processing the wafer to alert those methods and/or apparatus about the unacceptable BPSG deposition condition. If the determination at step 370 was YES, that further attempts at producing a desired BPSG conformality condition will be undertaken, the unacceptable BPSG deposition values are analyzed to determine which, if any, reflow controlling components should be controlled to attempt to achieve the desired BPSG conformality condition. After the analyses, relevant reflow controlling components, which correspond to the grid blocks with unacceptable BPSG deposition values, regulate the temperature of the respective wafer portions to a level employed in reheating and reflowing the relevant BPSG portion. The present iteration is then ended and the process returns to step 320 to perform another iteration.

The present invention provides for a system and method for regulating BPSG deposition and reflow. As a result, the present invention facilitates improving BPSG layer conformality, which in turn increases chip fabrication quality in accordance with the present invention.

Scatterometry is a technique for extracting information about a surface upon which a incident light has been directed. Information concerning properties including, but not limited to, dishing, erosion, profile, thickness of thin films and critical dimensions of features present on the surface can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N=n-jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 11:
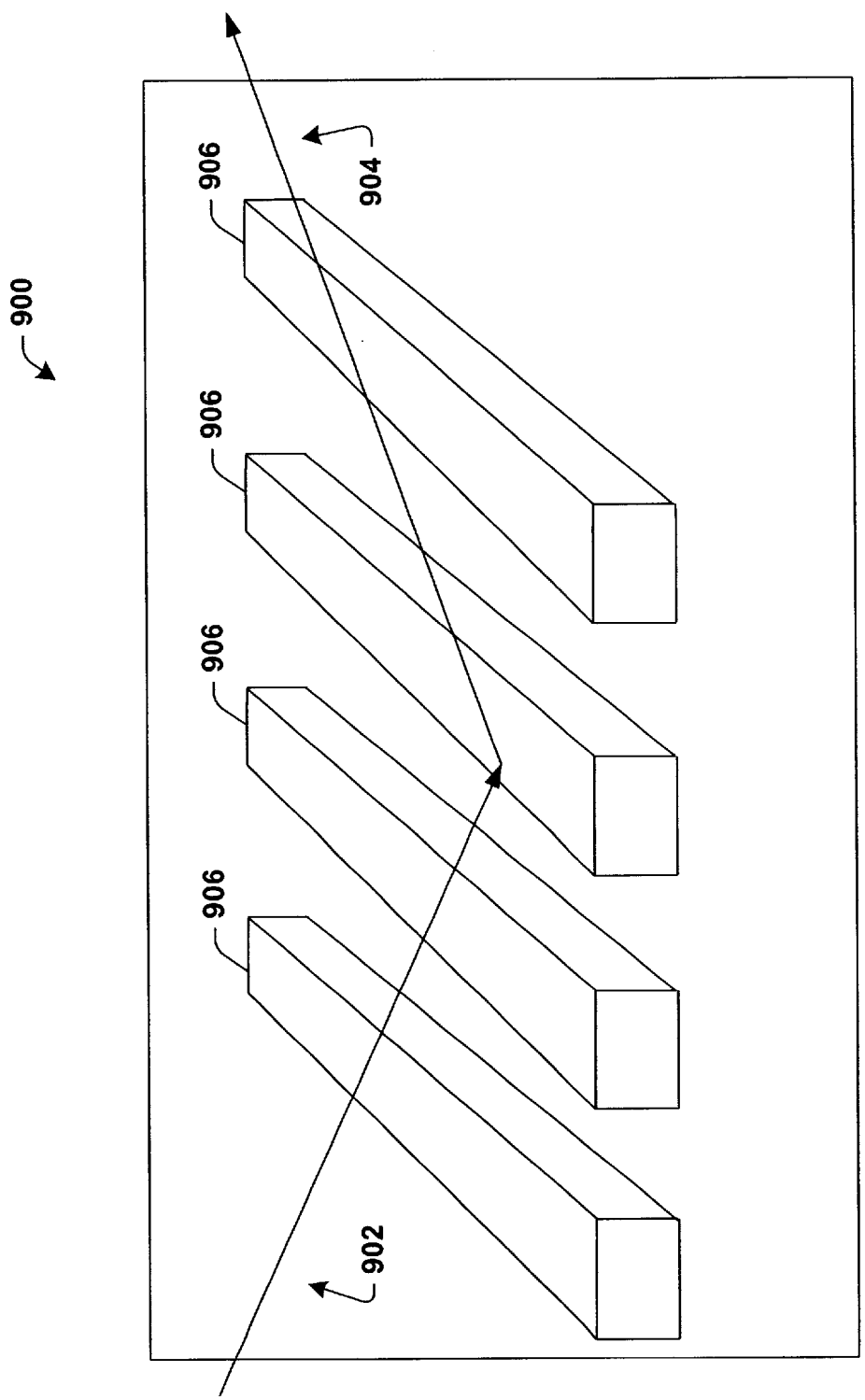
FIG. 11 is a simplified perspective view of an incident light reflecting off a surface, in accordance with an aspect of the present invention.
Figure 16:
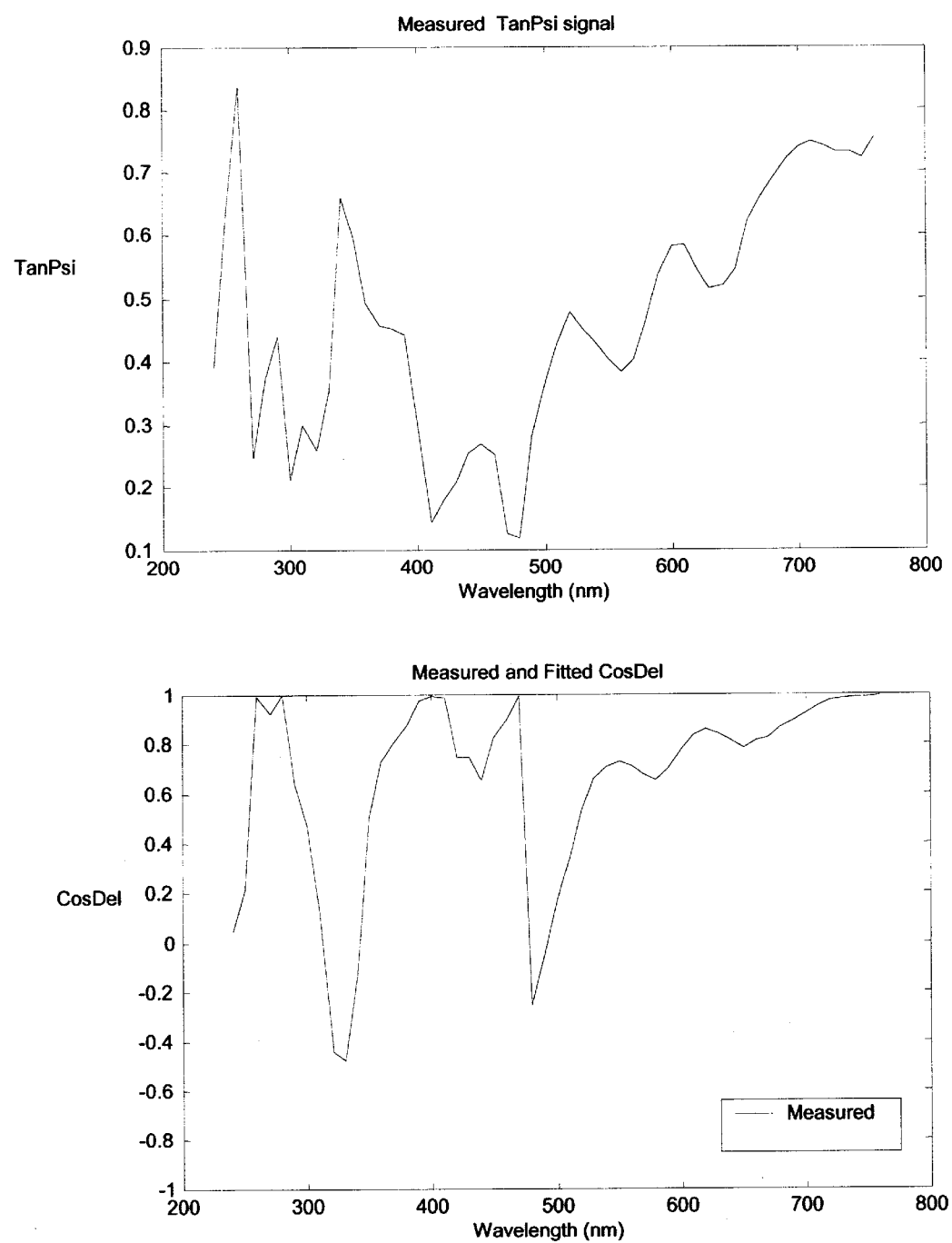
FIG. 16 illustrates phase and intensity signals recorded from a complex reflected and refracted light produced when an incident light is directed onto a surface, in accordance with an aspect of the present invention.

To illustrate the principles described above, reference is now made to FIGS. 11 through 16. Referring initially to FIG. 11, an incident light 902 is directed at a surface 900, upon which one or more features 906 may exist. In FIG. 11 the incident light 902 is reflected as reflected light 904. The properties of the surface 900, including but not limited to, thickness, uniformity, planarity, chemical composition and the presence of features, can affect the reflected light 904. In FIG. 11, the features 906 are raised upon the surface 900. The phase and intensity of the reflected light 904 can be measured and plotted, as shown, for example, in FIG. 16. The phase 960 of the reflected light 904 can be plotted, as can the intensity 962 of the reflected light 904. Such plots can be employed to compare measured signals with signatures stored in a signature library using techniques like pattern matching, for example.

Figure 12:
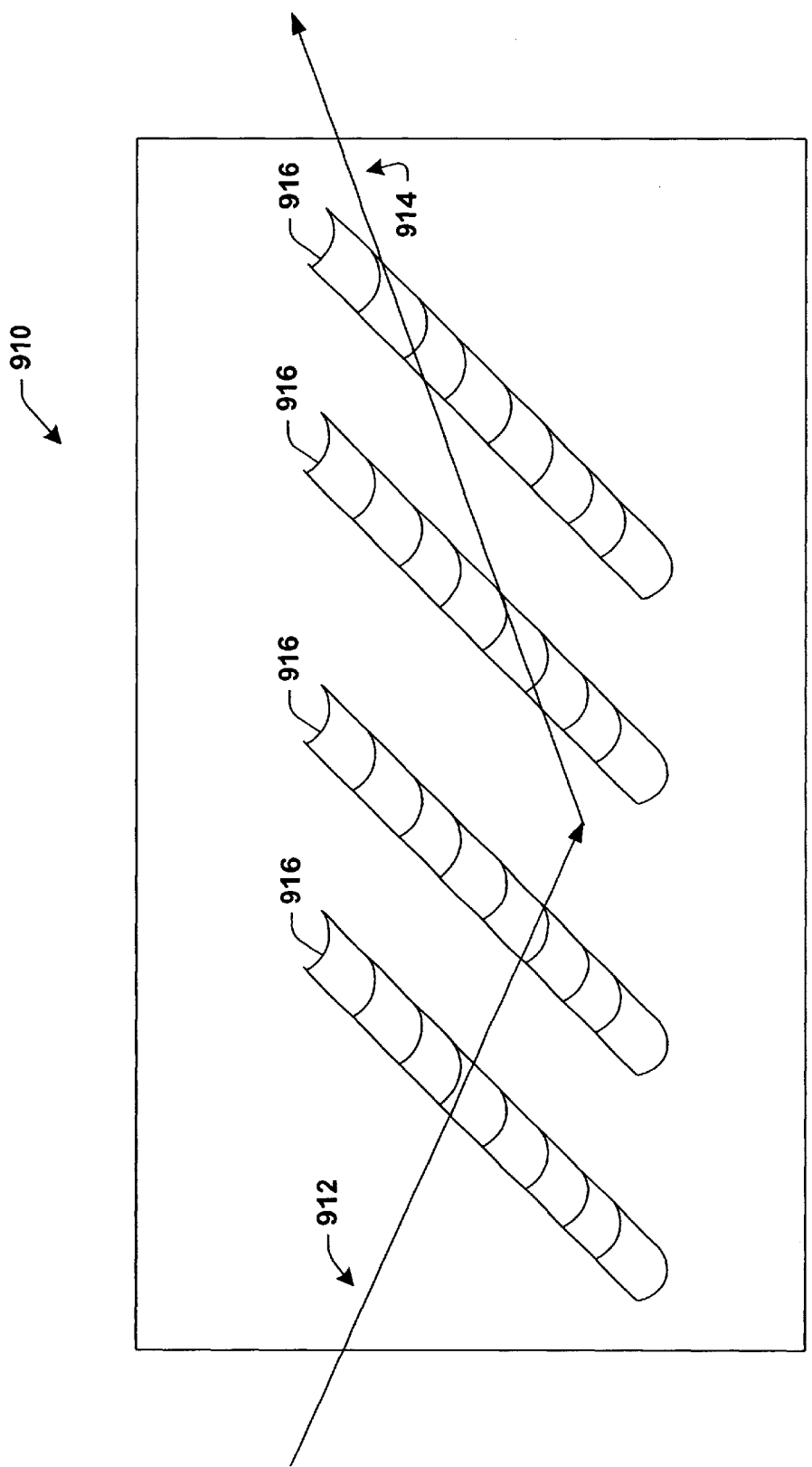
FIG. 12 is a simplified perspective view of an incident light reflecting off a surface, in accordance with an aspect of the present invention.

Referring now to FIG. 12, an incident light 912 is directed onto a surface 910 upon which one or more depressions 916 appear. The incident light 912 is reflected as reflected light 914. Like the one or more features 906 (FIG. 12) may affect an incident beam, so too may the one or more depressions 916 affect an incident beam. Thus, it is to be appreciated by one skilled in the art that scatterometry can be employed to measure features appearing on a surface, features appearing in a surface, and properties of a surface itself, regardless of features.

Figure 13:
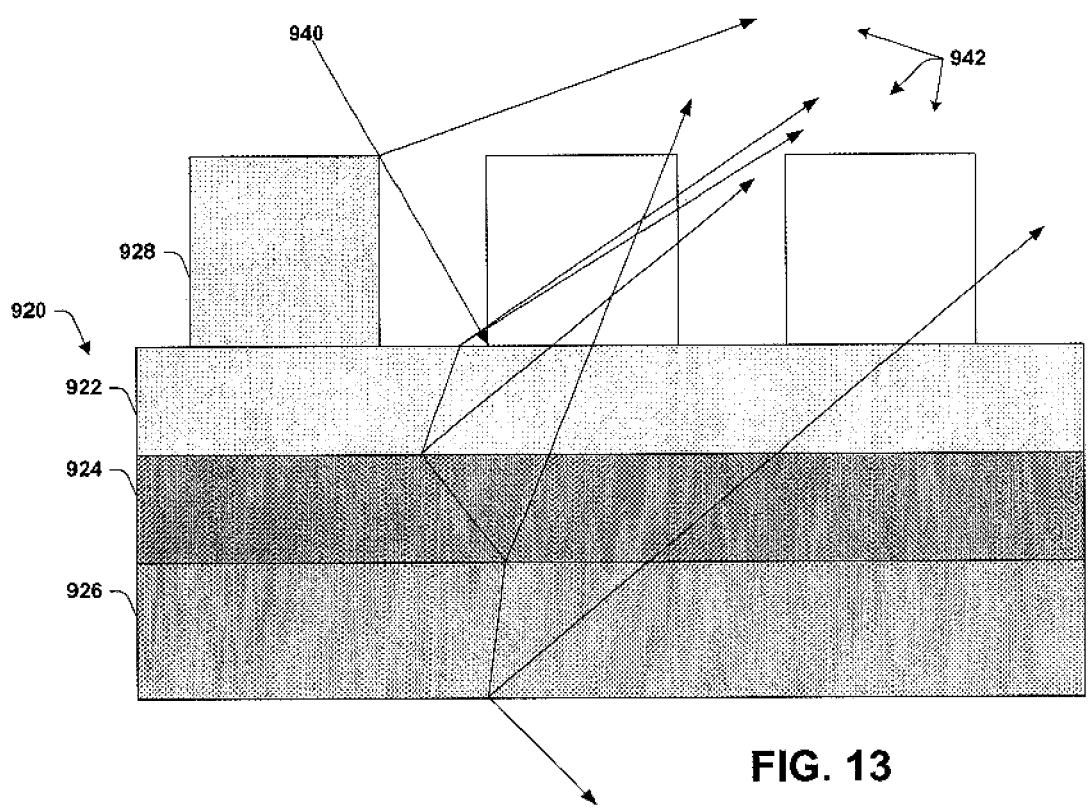
FIG. 13 illustrates a complex reflected and refracted light produced when an incident light is directed onto a surface, in accordance with an aspect of the present invention.

Turning now to FIG. 13, complex reflections and refractions of an incident light 940 are illustrated. The reflection and refraction of the incident light 940 can be affected by factors including, but not limited to, the presence of one or more features 928, and the composition of the substrate 920 upon which the features 928 reside. For example, properties of the substrate 920 including, but not limited to the thickness of a layer 922, the chemical properties of the layer 922, the opacity and/or reflectivity of the layer 922, the thickness of a layer 924, the chemical properties of the layer 924, the opacity and/or reflectivity of the layer 924, the thickness of a layer 926, the chemical properties of the layer 926, and the opacity and/or reflectivity of the layer 926 can affect the reflection and/or refraction of the incident light 940. Thus, a complex reflected and/or refracted light 942 may result from the incident light 940 interacting with the features 928, and/or the layers 922, 924 and 926. Although three layers 922, 924 and 926 are illustrated in FIG. 13, it is to be appreciated by one skilled in the art that a substrate can be formed of a greater or lesser number of such layers.

Figure 14:
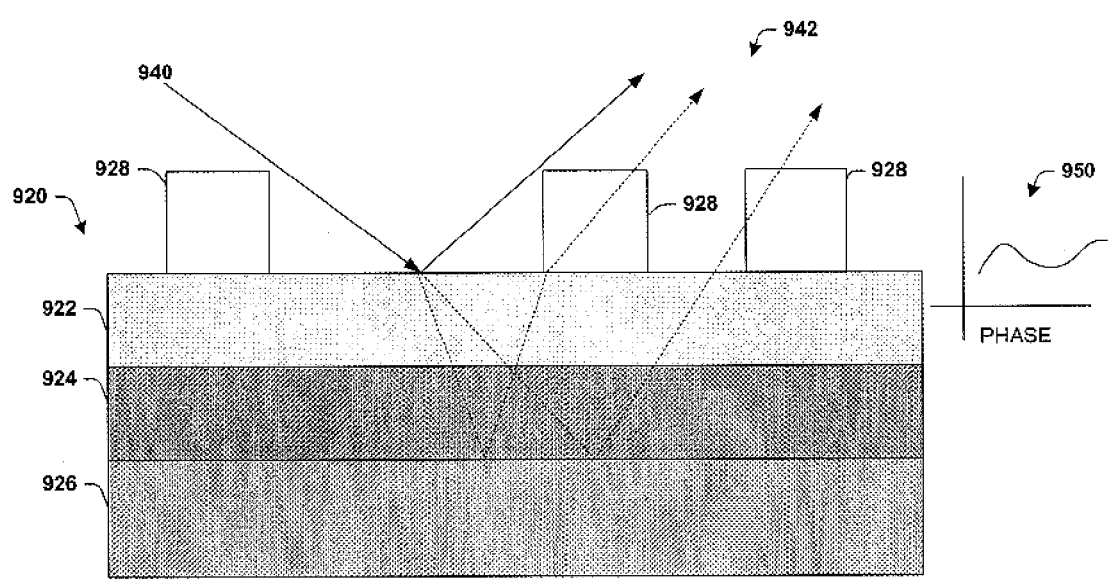
FIG. 14 illustrates a complex reflected and refracted light produced when an incident light is directed onto a surface, in accordance with an aspect of the present invention.
Figure 15:
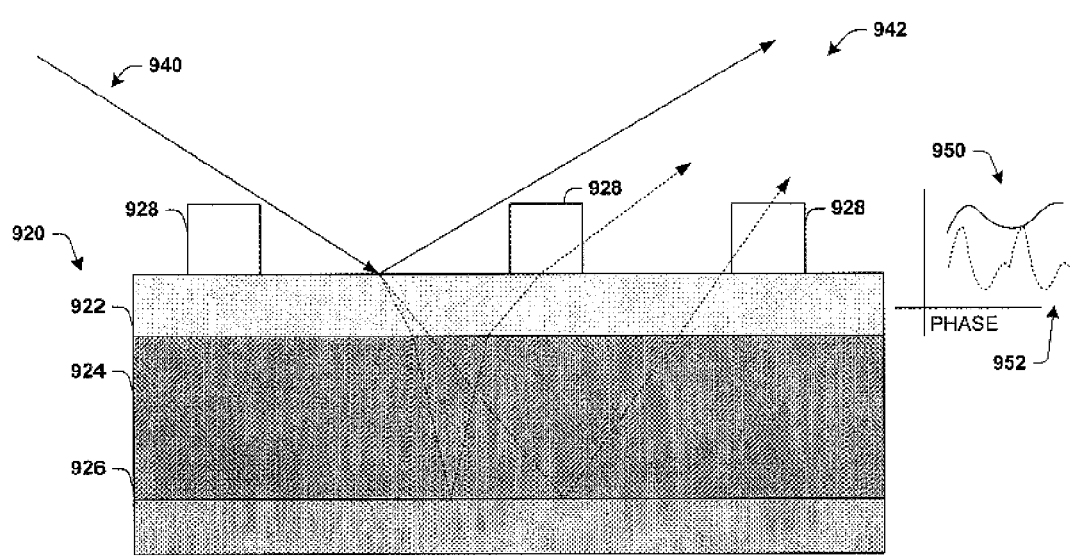
FIG. 15 illustrates a complex reflected and refracted light produced when an incident light is directed onto a surface, in accordance with an aspect of the present invention.

Turning now to FIG. 14, one of the properties from FIG. 13 is illustrated in greater detail. The substrate 920 can be formed of one or more layers 922, 924 and 926. The phase 950 of the reflected and/or refracted light 942 can depend, at least in part, on the thickness of a layer, for example, the layer 924. Thus, in FIG. 15, the phase 952 of the reflected light 942 differs from the phase 950 due, at least in part, to the different thickness of the layer 924 in FIG. 15.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system for monitoring and controlling boron phosphorous doped silicon oxide (BPSG) deposition and reflow, comprising:

at least one reflow controlling component operative to control the temperature of at least one portion of a wafer;

a reflow controlling component driving system for driving the at least one reflow controlling component;

a system for directing light to the at least one portion of the wafer;

a measuring system for measuring BPSG deposition parameters based on light reflected from the at least one portion of the wafer; and a processor operatively coupled to the measuring system and the reflow controlling component driving system, the processor receiving BPSG deposition data from the measuring system and the processor using the data to at least partially base control of the at least one reflow controlling component so as to regulate the temperature of the at least one portion of the wafer.

2. The system of claim 1, the measuring system further including a scatterometry system for processing the light reflected from the at least one portion of the wafer.

3. The system of claim 1, further comprising a measuring system for measuring BPSG deposition parameters based on light passing through the at least one portion of the wafer.

4. The system of claim 3, the measuring system further including a scatterometry system for processing the light passing through the at least one portion of the wafer.

5. The system of claim 2 or claim 4, the processor being operatively coupled to the scatterometry system, the processor analyzing data relating to BPSG deposition received from the scatterometry system, and the processor basing control of the at least one reflow controlling component at least partially on the analyzed data.

6. The system of claim 1, the processor mapping the wafer into a plurality of grid blocks, and making a determination of BPSG deposition conditions at the one or more grid blocks.

7. The system of claim 1, wherein the processor determines the existence of an unacceptable BPSG deposition condition for at least a portion of the wafer based upon a determined BPSG deposition value differing from an acceptable value.

8. The system of claim 7, wherein the processor controls the at least one reflow controlling component to regulate the temperature of at least one wafer portion.

9. A method for monitoring and controlling BPSG deposition and reflow, comprising:

defining a wafer as a plurality of portions;

depositing BPSG on the wafer;

directing light onto at least one of the portions;

collecting light reflected from the at least one portion;

analyzing the reflected light to determine the BPSG deposition on the at least one portion; and controlling at least one reflow controlling component to regulate the BPSG deposition and reflow of the at least one portion.

10. The method of claim 9, further comprising:

using a scatterometry system to process the reflected light.

11. The method of claim 9, further comprising:

collecting light passing through the at least one portion; and analyzing the passed through light to determine a BPSG deposition condition of the at least one portion.

12. The method of claim 11, further comprising:

using a scatterometry system to process the passed through light.

13. The method of claim 10 or 12, further comprising:

using a processor to control the at least one reflow controlling component based at least partially on data received from the scatterometry system.

14. A method for monitoring and controlling a BPSG deposition and reflow process, comprising:

partitioning a wafer into a plurality of grid blocks;

using a plurality of reflow controlling components to control the temperature of the wafer, each reflow controlling component functionally corresponding to a respective grid block;

determining the BPSG conformality of one or more portions of the BPSG, each portion corresponding to a respective grid block; and using a processor to coordinate control of the plurality of reflow controlling components, respectively, in accordance with determined BPSG conformality in the respective portions of the BPSG.

15. A system for monitoring and controlling a BPSG deposition and reflow process, comprising:

means for partitioning a wafer into a plurality of grid blocks;

means for sensing BPSG deposition of at least one of the plurality of portions of the wafer;

means for controlling the temperature of the respective wafer portions to control reheating and reflow of BPSG on the respective wafer portions; and means for selectively controlling the means for controlling the temperature to regulate the temperature of the respective wafer portions.

* * * * *